US009124777B2

(12) United States Patent
Van Leest et al.

(10) Patent No.: US 9,124,777 B2
(45) Date of Patent: Sep. 1, 2015

(54) DEVICE AND METHOD FOR EXTRACTING INFORMATION FROM CHARACTERISTIC SIGNALS

(75) Inventors: Adriaan Johan Van Leest, Eindhoven (NL); Gerard De Haan, Helmond (NL); Willem Verkruijsse, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/990,809

(22) PCT Filed: Jan. 4, 2012

(86) PCT No.: PCT/IB2012/050033
§ 371 (c)(1),
(2), (4) Date: May 31, 2013

(87) PCT Pub. No.: WO2012/093358
PCT Pub. Date: Jul. 12, 2012

(65) Prior Publication Data
US 2013/0271591 A1 Oct. 17, 2013

(30) Foreign Application Priority Data
Jan. 5, 2011 (EP) .................................... 11150151

(51) Int. Cl.
G06K 9/00 (2006.01)
H04N 7/18 (2006.01)
A61B 5/00 (2006.01)
A61B 5/024 (2006.01)

(52) U.S. Cl.
CPC ................ *H04N 7/18* (2013.01); *A61B 5/0064* (2013.01); *A61B 5/02438* (2013.01); *A61B 5/7207* (2013.01)

(58) Field of Classification Search
None
See application file for complete search history.

(56) References Cited

U.S. PATENT DOCUMENTS 4,166,454 A 9/1979 Meijer
8,666,116 B2 3/2014 Kirenko et al.
(Continued)

FOREIGN PATENT DOCUMENTS

JP 9262213 A 10/1997
JP 2005095581 A 4/2005
(Continued)

OTHER PUBLICATIONS

Becouze et al, "Measuring Facial Grimacing for Quantifying Patient Agitation in Critical Care", Department of Mechanical Engineering, University of Canterbury, New Zealand, Aug. 6, 2010, pp. 1-31.
(Continued)

*Primary Examiner* — Siamak Harandi

(57) ABSTRACT

The present invention relates to a device and a method for extracting information from detected characteristic signals. A data stream (76, 78, 80, 82) derivable from electromagnetic radiation (14) emitted or reflected by an object (11) is received and a plurality of characteristic index elements (50) varying over time can be extracted therefrom. The index elements (50) comprise physiological information (48) indicative of at least one at least partially periodic vital signal (12), and a disturbing signal component (58). For eliminating the disturbing signal component (58) to a great extent, the characteristic index elements (50) can be projected to a disturbance-reduced index element (64) having a distinct orientation in relation to a presumed orientation of the disturbing signal component (58). The disturbance-reduced index element (64) is chosen so as to reflect a dominant main orientation and length of the disturbing signal component (58) over time. Consequently, the mainly genuine physiological information (48) extracted from the data stream (76, 78, 80, 82) in this way can be utilized for determining the at least one at least partially periodic vital signal (12).

20 Claims, 4 Drawing Sheets

(56) References Cited

U.S. PATENT DOCUMENTS

| | | |
|---|---|---|
| 2008/0045847 A1 | 2/2008 | Farag et al. |
| 2009/0141124 A1 | 6/2009 | Liu et al. |
| 2009/0226071 A1* | 9/2009 | Schuler et al. ................. 382/133 |
| 2010/0179611 A1* | 7/2010 | O'Brien et al. .................. 607/17 |
| 2010/0228139 A1* | 9/2010 | Nanba et al. ................... 600/509 |

FOREIGN PATENT DOCUMENTS

| | | |
|---|---|---|
| WO | 2005030330 A1 | 4/2005 |
| WO | 2009124297 A1 | 10/2009 |
| WO | 2010100594 A2 | 9/2010 |
| WO | 2011042839 A1 | 4/2011 |

OTHER PUBLICATIONS

Pavlidis et al, "Interacting With Human Physiology", Science Direct, Computer Vision and Image Understanding, vol. 18, 2007, pp. 150-170.

Shlens, "A Tutorial on Principal Component Analysis", Center for Neural Science, New York University, Mar. 25, 2009, Version 1, pp. 1-16.

* cited by examiner

DEVICE AND METHOD FOR EXTRACTING INFORMATION FROM CHARACTERISTIC SIGNALS

FIELD OF THE INVENTION

The present invention relates to a device and method for extracting information from characteristic signals, wherein the characteristic signals are embedded in a data stream derivable from electromagnetic radiation, in particular wherein the data stream comprises a continuous or discrete signal including physiological information indicative of at least one at least partially periodic vital sign.

BACKGROUND OF THE INVENTION

WO 2010/100594 A2 discloses a method and a system for processing images of living beings. The method comprises the steps of:

- obtaining a sequence of digital images taken at consecutive points in time;
- selecting at least one measurement zone comprising a plurality of image points, wherein
- the step of selecting at least one measurement zone includes analyzing information based on pixel data of a plurality of image parts in at least one of the images, each image part including at least one image point, and selecting each measurement zone from contiguous parts determined to have similar characteristics; and
- for each measurement zone, obtaining a signal representative of at least variations in a time-varying average value of a combination of pixel values at at least a number of the image points for use in determining at least one of a presence and a frequency value of at least one peak in a spectrum of the signal corresponding to a frequency of a periodic physiological phenomenon.

This document further discloses several refinements of the method. In general, in the field of image processing enormous progress was made in that profound analyses of the recorded data were enabled. In this context, it could be envisaged to extract information from recorded data in a way as to enable detailed conclusions regarding the personality or even the well-being of an observed living individual.

However, as the recorded data, such as captured reflected or emitted electromagnetic radiation, especially recorded image frames, always comprises, beside of the desired signal to be extracted therefrom, further signal components deriving from overall disturbances, by way of example, such as noise due to changing luminance conditions or a movement of observed objects, a detailed precise extraction of the desired signals still poses major challenges for the processing of such data.

This applies in particular when amplitudes and/or nominal values of disturbing signal components are much larger than amplitudes and/or nominal values of desired signal components to be extracted. Potentially, the magnitude of difference between the respective components can be expected to even comprise several orders.

A possible approach to this challenge may be directed to providing well-prepared and steady ambient conditions when capturing a signal of interest in which the desired signal component is embedded so as to minimize disturbing signal components overlaying the signal. However, such laboratory conditions cannot be transferred to everyday field applications as high efforts and preparation work would be required therefor.

The required preparation might comprise, by way of example, installation and orientation of several standard light sources and, moreover, measures for fixation of the object to be observed in order to avoid disturbing movements responsible for an even larger noise level.

SUMMARY OF THE INVENTION

It is therefore an object of the present invention to provide a system and a method for extracting information from detected characteristic signals providing further refinements facilitating obtaining the desired signals with higher accuracy.

Furthermore, it would be advantageous to provide a system even adapted for enabling an extraction of the desired signals under considerably poor ambient conditions, e.g. small signal-to-noise ratio, varying luminance conditions and/or steady of even unsteady movements of the object to be observed.

In a first aspect of the present invention a system for extracting information from detected characteristic signals is presented, the system comprising:

- an interface for receiving a data stream derivable from electromagnetic radiation emitted or reflected by an object, the data stream comprising a continuous or discrete characteristic signal including physiological information, the physiological information being representative of at least one at least partially periodic vital signal,
- an extractor means for extracting the physiological information from the data stream, the extractor means deriving a plurality of characteristic index elements from the data stream, the plurality of characteristic index elements being indicative of the physiological information and a disturbing signal component, wherein the plurality of characteristic index elements is associated with a signal space representative of characteristics of the electromagnetic radiation, the signal space comprising a predetermined index element having a set orientation indicative of a reference physiological information, the predetermined index element being at least approximately determinable by an upstream determination of respective reference values,
- a converter means for converting the plurality of characteristic index elements by projecting them to a disturbance-reduced index element derived from a given orientation and length of the plurality of characteristic index elements, the disturbance-reduced index element having a distinct orientation in relation to a presumed orientation of the disturbing signal component, wherein the disturbance-reduced index element is determined by optimizing an expression with consideration of the orientation of the predetermined index element.

The present invention is based on the insight that, when aiming at an extraction of the desired vital signal, in general a poor signal-to-noise ratio has to be considered. Having this general ratio in mind, it is likely to assume that the signal component of interest, namely the characteristic index elements, generally comprises a major part indicative of noise and the like, namely the disturbing component, and a probably very small part indicative of the desired vital signal, namely the physiological information. As the disturbing signal component can be influenced by numerous disturbance sources, the position and orientation thereof with regard to the signal space cannot be accurately predicted in advance. However, the general orientation of the physiological information in the signal space can be, at least approximately, predetermined and embodied by the predetermined index element associated with the signal space. In other words, merely an expected nominal orientation, e.g. an axis or curve, of the physiological information can be determined by an upstream process. On the other hand, the signal to be detected comprises, beside of a small desired part, a major disturbing component the orientation, position and value of which are fairly unknown.

In this context, European patent application no. 09172337.9, in the name of the same applicant as the present invention, filed before and published after the priority date of the present application, proposes an enhancement of the extraction of the desired signals in that, in essence, a detected overall signal representative of the desired signal and noise is to be projected to a predetermined axis in a signal space, thereby eliminating noise orthogonal to this predetermined axis. The signal-to-noise ratio can be improved to a certain extent in this way. However, as a further refinement it would be desirable to further enhance this ratio by also eliminating signal components indicative of noise generally orientated parallel to the predetermined axis or line.

Considering available input variables and given constraints, it should be noted that it appears to be unlikely to provide a solution for the problem outlined above that is merely based on analytical and similar methods aiming at clear and unique results. In contrast, the present invention relies on methods of multivariate statistics in order to arrive at an approximate solution. Needless to say, also approximate solutions are considered to adequately improving the signal-to-noise ratio, therefore fairly facilitating the extraction of the desired vital signals. The characteristic signal is, so to say, analyzed in a way to detect a characteristic pattern of several characteristic index elements indicative of a main orientation of the overlaying disturbing signal components. Having at least approximately determined the main disturbance or noise orientation, the characteristic index elements can be projected to an element orthogonal to this determined main orientation, namely the so-called disturbance-reduced index element, thereby eliminating noise orthogonal thereto. Thus, a great improvement in noise reduction and signal quality can be achieved.

There exist several embodiments of the extractor means and the converter means. In a first, fairly simple embodiment both, the detector means and the converter means, are embodied by a processing unit, in particular a processing unit of a personal computer, which is driven by respective logic commands. Such a processing unit may also comprise suitable input and output interfaces.

However, in the alternative, each of the extractor means and the converter means can be embodied by a separate processing unit driven or driveable by respective commands. Hence, each respective processing unit can be adapted to its special purpose. Consequently, a distribution of tasks may be applied, wherein distinct tasks are processed, for instance, executed on a single processor of a multi-processor processing unit, or, again referring to a personal computer, image processing-related tasks are executed on an image processor while other operational tasks are executed on a central processing unit.

According to a preferred embodiment of the device for extracting information, the device further comprises an analyzing means for determining the temporal variation of the projected index element, and for detecting the at least one at least partially periodic vital signal represented by the physiological information.

Also the analyzing means can be embodied by a processing unit driven by logic commands. To this end, a separate processing unit, or a processing unit which is common for the extractor means, the converter means and the analyzing means can be utilized. The signal of interest, the at least one at least partially periodic vital signal, is represented, so to say, by a pulsation of the projected index element over time. A characteristic frequency underlying this pulsation can be considered highly indicative of the desired vital signal.

It should be noted that the projected index element still generally does not exactly coincide with the predetermined index element. This would only happen in case the determined main orientation of the disturbing signal components of the plurality of characteristics index elements should be orthogonal to the predetermined index element. If this would apply, already a mere projection of each of the plurality of characteristic index elements to the predetermined index element which, in this case, coincides with the disturbance-reduced index element would arrive at a fairly precise determination of the at least one at least partially periodic vital signal. However, even if the predetermined index element and the disturbance-reduced index element form an angle, preferably an acute angle, the projected index element (projected to the disturbance-reduced index element) enables an accurate determination of the at least one at least partially periodic vital signal as disturbing signal components indicative of noise are eliminated therefrom, at least to a considerable extent. In case mainly the frequency of the temporal variations of the projected index element is to be analyzed in order to detect the signal of interest, the mere length of the projected index element which differs from the assumed length of the physiological information when aligned with the predetermined index element does not lead to a wrong or distorted result of a frequency analysis as the frequency underlying the temporal pulsation is not influenced.

Alternatively, it would be further advantageous to present a device further refined in that the amplitude of the projected index element is corrected with a factor depending on the angle between the disturbance-reduced index element and the predetermined index element.

In this connection, according to a further improvement of the embodiment the analyzing means is further adapted to compensate an angular offset between the projected index element and the predetermined index element having the set orientation.

The compensation can be performed by trigonometric calculations. In this manner, the characteristic index element can be accurately separated into the disturbing signal component and the physiological information, which accurately represents the signal component of interest. In other words, the physiological information can be almost completely restored from the noise-containing original characteristic index element.

According to a preferred embodiment of the device for extracting information the plurality of characteristic index elements is a set of difference vectors representing temporal variations of the continuous or discrete characteristic signal in the signal space.

In this connection, WO 2010/100594 A2 and European patent application no. 09172337.9 basically exemplify methods and devices for detecting such characteristic index elements and, moreover, methods and devices for analyzing a processed signal derived therefrom so as to, in principle, arrive at desired vital signals.

According to an even further embodiment, the device for extracting information further comprises a sensor means for detecting an electromagnetic radiation within at least one particular wavelength range selected from the group consisting of visible light, infrared light, and ultraviolet radiation, the sensor means being connectable to the interface.

In the alternative, data already captured and stored can be delivered to the interface and processed by the device. When observing a living being, in particular an animal or, more particularly, a human being, vital signals can be derived from slight variations in the radiation emitted, e.g. infrared light, and/or reflected, e.g. visible light and ultraviolet radiation. For everyday application it is appreciated if substantially visible light is detected and analyzed. To this end, beside of common natural or artificial light sources no further radiation sources are required and/or have to be considered during analysis.

This embodiment can be further developed in that the sensor means comprises a camera adapted for capturing a signal within a signal space selected from the group consisting of RGB, sRGB, Rg chromaticity, HSV, HSL, CMYK, YPbPr, YCbCr, and xvYCC.

In other words, video cameras providing a sufficient color depth, even so-called webcams, can be utilized for observing the object of interest and recording the data stream to be analyzed. It goes without saying that also derivates of the named signal space types may be utilized, such as logRGB. It can be further envisaged to combine several distinct signal spaces at least partially so as to provide a broader spectral basis for the required analyzing processes.

In this context, as an alternative, also a signal space can be envisaged which comprises wavelength ranges of visible light and of infrared light. In this way, the device can be suitably adapted to varying overall conditions such as greater changes in luminance conditions, or even day and night changes.

According to a further embodiment of the invention the signal space can be further transformed by taking the logarithm of the detected plurality of characteristic index elements. In other words, also the scale of spectral components or characteristics of the electromagnetic radiation represented by the signal space can be converted to a logarithmic scale. To this extent, subsequent calculations in the signal space can be facilitated. Further, a range of several magnitudes of values of input signals can be detected and processed while still enabling a clear overview and understanding of the representation thereof is enabled.

According to an even further embodiment of the device for extracting information the at least one at least partially periodic vital signal is selected from the group consisting of heart beat, respiration rate, and heart rate variability.

Needless to say, it is appreciated if the respective vital signal types can be converted into one another by applying respective conversion and analyzing steps.

The named vital signals are related to blood circulation which can be observed by the sensor means when recording a sequence of images representing an indicative area of the object of interest, e.g. a human being. Slight variations of electromagnetic radiation emitted or reflected by the observed object can be represented, when analyzing the recorded data stream, by the derived plurality of characteristic index elements. However, as mentioned above, beside of the slight variations also disturbing signal components are embedded in the plurality of characteristics index elements.

According to a further embodiment of the device for extracting information the signal space is a normalized color space, wherein at least one degree of freedom is at least temporarily compensated by a normalization process.

In practice, by way of example, the "pulsation" of the plurality of characteristics index elements comprising the physiological information can describe a three-dimensional curve in the signal space. Analysis and calculation can be simplified to a great extent in case said three-dimensional curve can be converted to a two-dimensional curve, or even a two-dimensional straight line.

In this context, it is further preferred if the signal space is a normalized two-dimensional color space, wherein a luminance normalization and a color normalization is carried out.

According to an even further embodiment of the device for extracting information, the extractor means further comprises a normalizing means for transferring the data stream into the signal space by normalizing actual luminance values embedded in the data stream by applying a respective determined combination of primary colors to color-representative components of the data stream, and/or by normalizing the color intensity of the data stream by applying respective temporal mean values of the data stream to actual values of color-representative components thereof.

According to another even further preferred embodiment of the device for extracting information, the analyzing means further comprises a filter means for filtering the data stream and for enhancing a signal component at a bandwidth between 0.2 Hz and 10 Hz, preferably between 0.5 Hz and 3.5 Hz.

In this way, even further disturbing signal components non-indicative of the desired vital signals can be removed from the data stream. In this context, it should be mentioned that the luminance normalization step, the color normalization step and the filtering step can be applied to the data stream either each step alone or in any combination of two or three steps thereof.

According to a further preferred embodiment of the device for extracting information, the converter means is adapted for determining the disturbance-reduced index element by defining a dataset comprising a set of characteristic index element values derived by the extractor means, and by performing a transformation, preferably a substantially orthogonal linear transformation, of the dataset to a coordinate system wherein a dominant component thereof is aligned with an axis of the coordinate system, and wherein the dominant component coincides with the disturbance-reduced index element.

By applying such a statistical analysis to the plurality of characteristics index elements the disturbance-reduced index element can be determined, even though a lack of input data and given constraints impedes an analytical solution. This embodiment can be further developed in that the disturbance-reduced index element is determined by minimizing the energy of the projected characteristic index elements over a temporal interval.

According to a further embodiment, the disturbance-reduced index element is determined by performing a principal component analysis on the plurality of characteristic index elements or their derivates in a temporal interval, and by selecting the element resulting therefrom which has the smallest eigenvalue and correlates significantly with the known predetermined index element as the disturbance-reduced index element.

In the alternative, it could be further advantageous if a weight function is applied for determining the disturbance-reduced index element so as to converge the disturbance-reduced index element to the predetermined index element.

In a further aspect of the present invention a method for extracting information from detected characteristic signals is presented, comprising the steps:

receiving a data stream derivable from electromagnetic radiation emitted or reflected by an object, the data stream comprising a continuous or discrete characteristic signal including physiological information, the physiological information being representative of at least one at least partially periodic vital signal, extracting the physiological information from the data stream by deriving a plurality of characteristic index elements from the data stream, the plurality of characteristic index elements being indicative of the physiological information and a disturbing signal component, wherein the plurality of characteristic index elements is associated with a signal space representative of characteristics of the electromagnetic radiation, the signal space comprising a predetermined index element having a set orientation indicative of a reference physiological information, the predetermined index element being at least approximately determinable by an upstream determination of respective reference values, converting the plurality of characteristic index elements by projecting them to a disturbance-reduced index element derived from a given orientation and length of the plurality of characteristic index elements, the disturbance-reduced index element having a distinct orientation in relation to a presumed orientation of the disturbing signal component, wherein the disturbance-reduced index element is determined by optimizing an expression with consideration of the orientation of the predetermined index element.

Advantageously, the method can be carried out utilizing the device for extracting information of the invention.

According to an even further aspect of the invention a computer program is presented, the computer program comprising program code means for causing a computer to carry out the steps of the method for extracting information of the invention when said computer program is carried out on a computer.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
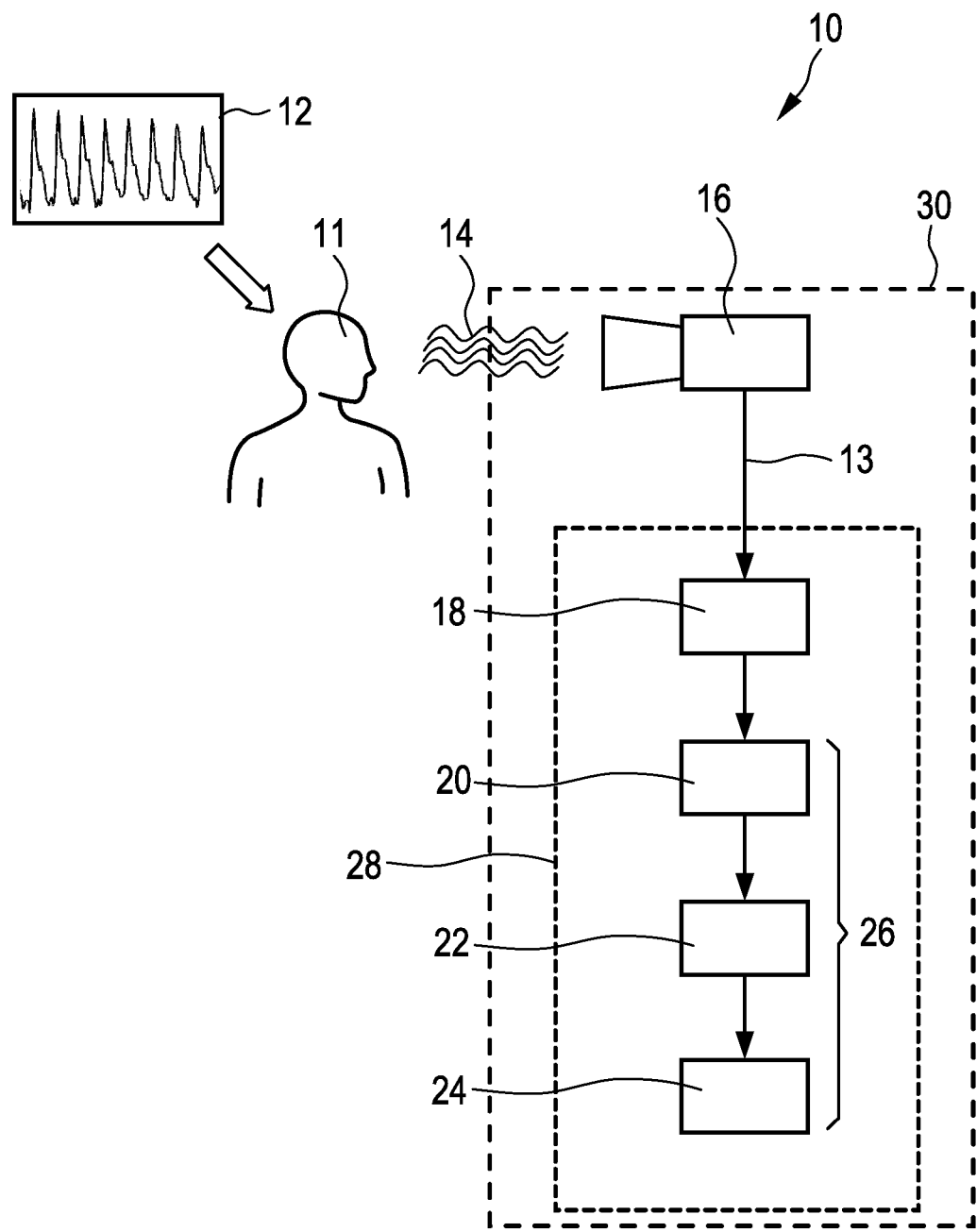
FIG. 1 shows a schematic illustration of a general layout of a device in which the present invention can be used.

Recently, unobtrusive monitoring of vital signs, such as, by way of example, heartbeat, heart rate variability and respiratory rate, using a sensor, such as a camera, or remote photoplethysmography devices, has been demonstrated. Basically, the underlying algorithms track an average signal emitted or reflected by a person or, in general, a living being, for instance, the color or tone of the skin of the observed object. The captured signal may vary over time with the blood volume and blood oxygenation. In general, however, this method is susceptible to motion of the object to be observed or to motion of the sensor with respect to the camera, further to local variations in the signal of interest, e.g. the skin tone, and illumination level changes and/or spectrum changes which are generally suspected of adversely affecting the monitoring result. In other words, the signal to be extracted is embedded in a captured signal having a poor, i.e. reasonably small, signal-to-noise ratio.

In this context, further measures are proposed to enhance the extraction of the signal of interest from the noise-containing overall signal by improving the robustness of the embedded vital signal indicative of the vital sign of interest. When aiming at an analysis of captured sequences of image frames, in general, this can be achieved by normalizing the average skin-tone in a time-interval, thus eliminating the effect of slow changes in the illumination spectrum and slow changes in the average skin-tone occurring due to motion. Moreover, the effect of local brightness variations can be eliminated by an illumination normalization leveling thereby reducing the influence of unsteady ambient lighting conditions.

The remaining variations over time of the detected signal, e.g. the skin tone color, under, so to say, normalized color conditions and normalized local illumination conditions, is assumed to reflect the variation of the vital signal of interest at least to a considerably extent. When further mapping this preprocessed signal to a signal space which comprises a predetermined index element, e.g. a so-called heart beat axis, which is supposed to at least approximately represent the assumed range or orientation of the signal of interest, the preprocessed signal can be projected thereon. In this way, noise-containing signal components still remaining in the preprocessed signal can be eliminated that are orthogonal to the predetermined element.

When taking the approach to assess vital signals by substantially deriving them from skin color changes over time, it has to be considered that, as a major challenge in this regard, the skin of a living being, in particular a human being, is a complex optical layer. Substantially, skin is composed of a thin surface layer, the epidermis, and the dermis, which is a thicker layer placed under the epidermis. Generally, light reflection of the skin takes place at the epidermis surface where merely a small part, e.g. about approximately 5%, of incident light is reflected. The remaining part of the incident light is entering the skin where it is absorbed and scattered within the skin layers. In other words, the epidermis mainly absorbs light; it has the properties of an optical filter, wherein the light is transmitted depending on its wavelength and the melanin concentration in the epidermis, i.e. the "color" of the skin. Light is further scattered in the dermis and either remitted as diffuse reflectance or absorbed in the dermis, most likely by blood or hair. The diffusely reflected light contains the signal since its intensity is temporally modulated by the periodic changes in blood volume fraction. The absorption is mainly dependent on the content of blood and its ingredients such as hemoglobin, bilirubin, and beta-carotene. Advantage is taken of these characteristics in that small variations of skin tone details, e.g. due to blood circulation, can be detected applying image processing methods.

In this connection, it can be envisaged to carry out a vital signal detection by adopting a sensor means, e.g. a camera, taking images of an area of the observed object which is assumed to be highly indicative of the desired signal. By way of example, the cheek of a person can fairly represent blood circulation over time and vital signals related thereto. To this end, pixel averages of the region of interest can be calculated and analyzed so as to determine at least partially periodic variations of the signal. The area of interest can be selected manually or by carrying out algorithms addressed to a detection of highly-representative skin regions.

It goes without saying that also stored data, e.g. image sequences or video data, already recorded can be utilized as input data to be analyzed in order to detect the presence of vital signals therein.

In principle, heart beat detection with a video camera, or remote PPG, can be applied as follows: blood-volume variations in the skin, due to the heart beat, cause color variations over time of the skin. A respective skin area can be detected and recorded accordingly. Averaging of selected pixels representative of the skin area in a sequence of image frames, detecting the averaged signal and tracking it over time can lead to a signal form, i.e. a waveform, from which the heart beat or, in general, another vital signal can be obtained.

However, as mentioned above, such a so-called basic system faces the challenge that the heart beat is not the only cause of variations in the extracted signal. Slight movements of the skin relative to the camera, i.e. the sensor means, and temporal illumination changes can be considered the main source of noise that can easily exceed the amplitude of the pure heart beat signal by orders of magnitude.

Again, when assessing vital signals by substantially deriving them from skin color changes over time captured by means of a camera, it can be envisaged that, for a known spectrum of the illumination, a known sensitivity of color filters in the camera and a known color filtering effect of the skin, it could be feasible to improve the signal-to-noise ratio, as the color change of interest can be predicted to lie on a known vector in the color space. By projecting the measured signal on this vector, it is possible to eliminate artifacts that lead to noise orthogonal to this vector.

When further aiming at an extraction of the heart beat signal from spatially averaged skin-reflected light or radiation, it is appreciated to eliminate the effect of the time-varying spectrum of the illumination, which can change the direction of the heart beat signal in the signal space and can be caused, in general, by motion in an environment with spectrally different light sources, or motion relative to colored reflecting surfaces.

Furthermore, an elimination of the space-varying effect of the local skin-tone can be desirable, which can result from the fact that not always the same skin-tone positions are averaged, again possibly induced by motion and a somehow imperfect skin-tone detection.

Addressing the time-varying spectrum of the illumination, it can be envisaged to transform the signal space used by the sensor means, e.g. the color space, to a normalized signal space in which relatively slow color changes that are, in principle, not of interest have no effect. A further step to be carried out either subsequently to, prior to, or along with the luminance normalization, is based on the insight, that complex motion of the object to be observed, and/or of the camera with respect to the object, renders it difficult, or even impossible, to track the location of a pixel area of interest. Since a greater area of skin-pixels exhibits the color variation due to heart beat and/or blood oxygenation it could be advantageous to track merely the changes in the average value of the skin-pixels of a so-called pattern having a variable composition due to motion and so on. To this end, while motion itself may cause brightness variations, it is further proposed to normalize the brightness of individual skin-pixels prior to averaging them.

Again, needless to say that the order of the two steps can be selected at will and both options contribute to an improved signal-to-noise ratio.

The vital signal extraction from the temporal variations of the average normalized skin pixels can be further enhanced by projecting the detected signal on an at least approximately fixed predetermined index element, e.g. an empirically determined heart beat vector, and by applying a band-pass filtering to the extracted signal form. Such post-processing takes advantage of the fact that the frequency of the vital signals of interest lies generally within a known frequency range.

A further advantage of the two normalization steps is that the resulting skin-tone pixels eventually should resemble each other to a great extent, i.e. outliers, e.g. based on non-human artifacts, remaining in the signal form, e.g. due to inaccurate initial skin-tone detection, can be easily detected and eliminated.

It should be noted that throughout this document vectors and matrixes are not necessarily denoted by separate vector arrows in the continuous text part. In particular, it is understood that the person skilled in the art is aware of whether a scalar value or a vector value is recited.

By way of example, blood volume changes in the skin of living beings, e.g. due to heart beat, can be assumed to cause color changes in electromagnetic radiation reflected or emitted by the skin. Obviously, it is apparent, that reflected light can be utilized to derive the input data of interest therefrom. When viewed with a multi-spectrum camera, e.g. sensitive in the range of RGB or similar color spaces, or, in general, signal spaces, the registered color change $H_c$ at a position x and at time t, $$\vec{H}_c(\vec{x}, t) = \frac{d\vec{I}_c(\vec{x}, t)}{dt} = \frac{d}{dt}\begin{bmatrix} R_c(\vec{x}, t) \\ G_c(\vec{x}, t) \\ B_c(\vec{x}, t) \end{bmatrix}, \quad (1)$$

is influenced by the spectrum of the illumination source $\vec{I}_l(t) = [R_l(t) G_l(t) B_l(t)]^T$, the primary color filters $\vec{F}_c(t) = [F_{rc}(t) F_{gc}(t) F_{bc}(t)]^T$ of the camera and the local color of the skin covering the changing blood volume $\vec{F}_s(\vec{x}) = [F_{rs}(\vec{x}) F_{gs}(\vec{x}) F_{bs}(\vec{x})]^T$. It can be further assumed that the spectrum of the illumination $I_l$ does not substantially vary in a spatial sense, and the local skin-tone $F_s$ does not temporally vary, except for the desired vital signal.

Since the detected color change $H_c$ due to varying vital signals, in the present example, more accurately, the blood volume, is influenced and to some extent affected by both the local skin-tone and the time-varying illumination spectrum h, a multiplicative process has to be addressed to. Hence, it is appreciated if some normalization measures are applied for the sake of simplicity.

To this end, in a first step, the color space can be normalized by dividing the instantaneous spectral components, e.g., RGB-components, of the color vector $I_c$ by corresponding time-averages of the red, green and blue values, e.g., in case RGB or a similar signal space is applied:

$$\vec{I}_n(\vec{x}, t) = \begin{bmatrix} R_n(\vec{x}, t) \\ G_n(\vec{x}, t) \\ B_n(\vec{x}, t) \end{bmatrix} = \begin{bmatrix} \dfrac{R_c(\vec{x}, t)}{\overline{R_c}(t)} \\ \dfrac{G_c(\vec{x}, t)}{\overline{G_c}(t)} \\ \dfrac{B_c(\vec{x}, t)}{\overline{B_c}(t)} \end{bmatrix}, \quad (2)$$

wherein, considering the present sample determination, $\overline{R}_c(t)$, $\overline{G}_c(t)$, and $\overline{B}_c(t)$ correspond to the mean red, mean green, and mean blue values, respectively, in a region of interest, e.g. a pattern of skin pixels, X over time t:

$$\overline{R}_c(t) = \frac{1}{2\epsilon|X|} \int_{z=t-\epsilon}^{t+\epsilon} \int_X R_c(\vec{x}, z) d\vec{x} dz, \quad (3)$$

$$\overline{G}_c(t) = \frac{1}{2\epsilon|X|} \int_{z=t-\epsilon}^{t+\epsilon} \int_X G_c(\vec{x}, z) d\vec{x} dz,$$

$$\overline{B}_c(t) = \frac{1}{2\epsilon|X|} \int_{z=t-\epsilon}^{t+\epsilon} \int_X B_c(\vec{x}, z) d\vec{x} dz,$$

wherein |X| corresponds to the area of this region of interest X. The color change $H_n(x, t)$ in this normalized color space due to the vital signal of interest, e.g. the heartbeat, can be determined as follows:

$$H_n(\vec{x}, t) = \frac{d\vec{I}_n(\vec{x}, t)}{dt}, \quad (4)$$

insofar the color change $H_n(x, t)$ is not affected by a time-varying spectrum of the illumination.

In a time-discrete system which can be denoted by an additional subscript d in the expressions, wherein t can take the following values t=0, 1, 2, ..., n, and x corresponds to a pixel position, the color normalization eventually could read as follows:

$$\vec{I}_{n,d}(\vec{x}, t) = \begin{bmatrix} R_{n,d}(\vec{x}, t) \\ G_{n,d}(\vec{x}, t) \\ B_{n,d}(\vec{x}, t) \end{bmatrix} = \begin{bmatrix} \dfrac{R_{c,d}(\vec{x}, t)}{\overline{R_{c,d}}(t)} \\ \dfrac{G_{c,d}(\vec{x}, t)}{\overline{G_{c,d}}(t)} \\ \dfrac{B_{c,d}(\vec{x}, t)}{\overline{B_{c,d}}(t)} \end{bmatrix}, \quad (5)$$

wherein $R_{c,d}(x, t)$, $G_{c,d}(x, t)$, and $B_{c,d}(x, t)$ correspond to the red, green, and blue values of pixel x in time t, e.g. represented by respective image frames. The values $\overline{R}_{c,d}(t)$, $\overline{G}_{c,d}(t)$, and $\overline{B}_{c,d}(t)$ correspond to the mean red, mean green, and mean blue values of the respective summarized pattern, namely the region of interest in frame t, respectively. Further, the color change $H_{n,d}(x, t)$ in this normalized color-space due to the heart beat can be approximated by:

$$\vec{H}_{n,d}(\vec{x}, t) = \frac{\vec{I}_{n,d}(\vec{x}, t) - \vec{I}_{n,d}(\vec{x}, t-1)}{\vec{I}_{n,d}(\vec{x}, t) + \vec{I}_{n,d}(\vec{x}, t-1)}. \quad (6)$$

The exemplified step can cause a normalized, neutral, e.g. gray, color for the skin tone pixels, which can be considered being generally independent of the illumination source spectrum slowly varying compared with the heart beat, and of the filtering of the blood volume changes by the skin, i.e. of the filtering of the changes of reflected light induced by the blood volume changes. Consequently, the vital signal of interest can be, so to say, enhanced in relation to the remaining noise-containing overall signal. In this context, is should be noted that the respective divisions applied to RGB values outlined above can be replaced by subtractions when converting RGB values into a log RGB signal space.

In a further step, that may follow or precede the above step, the illumination level can be normalized so as to eliminate changes thereof that may be caused, in general, by motion of the object to be observed and/or of the camera, or by overall changes in illumination conditions. By way of example, the illumination level, for a given skin tone pixel, may change from one image to the next due to motion. Further, the local transmittance, reflectivity and absorption, or, in general, optical properties, of the skin may vary for several reasons. Since, again due to motion effects, not always the same skin pixels can be drawn for creating the pattern the average value determination is based upon, it would be very advantageous to eliminate these local illumination differences.

To normalize the amplitude, i.e. to become independent of varying local brightness levels and local transmission grades of the skin, it is envisaged to divide the local pixel values by a linear combination of their RGB-components:

$$\vec{I}_b(\vec{x}, t) = \frac{1}{\alpha R_n(\vec{x}, t) + \beta G_n(\vec{x}, t) + \gamma B_n(\vec{x}, t)} \vec{I}_n(\vec{x}, t). \quad (7)$$

In this way, the effect of capturing different skin pixels, and of capturing differently illuminated skin pixels in different subsequent image frames can be reduced to a large extent. To this end, it can be assumed that all primary colors are affected with the same percentage by the differences named above. Therefore, every linear combination of R, G, and B can be used and can lead to an improved result. In theory, the optimal choice of α, β, and γ can be considered a combination thereof that causes the resulting normalized pixels to lie in a plane parallel to the heart beat vector in the normalized color space. In practice, indeed, also other combinations can be applied, though leading to a somehow reduced amplitude of the heart beat signal, compared with the optimal linear combination, but, in general, there is no substantially adverse value for α, β, and γ.

Another further contribution to improve the robustness of the signal extraction by enhancing the signal-to-noise ratio is based on the fact that in the normalized signal space, e.g. a color space, such as the RGB color space, the variation of captured signals due to heart beat and/or blood oxygenation, namely the color variations, are somehow associated with a curve, e.g. a line or axis, in the utilized signal space. In other words, it can be assumed that, in general, the signal of interest is represented by a pulsation between two points along a curve or line indicative of the desired wave form of the signal of interest. This curve or line can be designated as a so-called heart beat line or axis which can be, at least approximately, predetermined by empirical studies and/or analytical methods.

Preferably, the captured and preprocessed signals can be projected to the heart beat line or axis thereby eliminating noise which is orientated orthogonal to this line. In case the signal space is normalized, in particular when the remaining signal space is a two-dimensional signal space, also the predetermined curve or line can be transferred into the resulting normalized signal space, e.g. into a plane. In this context, it would be further advantageous to apply a luminance normalization to the signal space of interest taking into account the given orientation of the predetermined index element so as to arrive at a normalized signal space which is aligned with the predetermined index element, at least to a certain extent. In this manner, the projection to be applied to the predetermined index element can be carried out avoiding a considerable loss of signal, e.g. an excessive compression due to a large angle between the original predetermined index element and the resulting predetermined index element transferred to the normalized signal space. According to another embodiment, it is envisaged to apply the two normalization steps, and subsequently, the projection step to the captured data comprising the vital signal of interest. In a further preferred embodiment, subsequent post-processing steps can be applied to the signal obtained from the input data comprising, by way of example, band pass filtering and/or Fourier domain analysis so as to arrive at a precise determination of an enhanced and distinct output signal, e.g. at a waveform indicative of a desired heart rate or frequency.

However, when projecting the vital sign indicative signal, whether normalized or not, to the predetermined index element, e.g. the so-called heart beat axis, mainly noise-containing signal components orientated orthogonal to said predetermined index element can be eliminated. Still, however, noise-containing signal components at least partially orientated parallel to or aligned with the predetermined index element remain in the signal. As mentioned above, when assessing vital signals embedded in captured data derivable from electromagnetic radiation emitted or reflected by an object, it can be expected that noise-indicative components are substantially larger than further components thereof indicative of vital signals. Therefore, even when applying the projection directed to the predetermined index element to the respective signal, the resulting processed improved signal, though having an improved signal-to-noise ratio, is probably still furnished with a main component primarily indicative of noise.

It would be further advantageous to modify the projection in a way as to further improve the signal-to-noise ration in that also noise-containing signal components that are not orientated orthogonal the predetermined index element they were to be initially projected to can be eliminated or at least reduced to a certain extent.

In this context, a refinement can be envisaged which is directed to the projection of the characteristic index elements to the disturbance-reduced index element. In the event that the distortion, i.e. the noise-containing signal component, is not orthogonal to the predetermined index element, e.g. the known heart beat line or axis, the signal-to-noise ratio can be even further improved when projecting the characteristic index elements to a so-called disturbance-reduced index element arranged in an orientation at least approximately orthogonal to a main orientation of the distortion. In this way, in practice, the named distortion can be reduced while, at the same time, the signal of interest, the physiological information, if at all, is merely compressed or stretched, i.e. has a reduced or enlarged amplitude, in case the distortion is somehow orientated parallel to the heart beat axis. Moreover, when the angle between the predetermined index element and the disturbance-reduced index element is known, the amplitude loss can be determined and corrected.

In other words, this refinement is based on the insight that, when projecting the characteristic index elements to the disturbance-reduced index element rather than to the predetermined index element which is indicative of the orientation of the signal of interest the distortion can disappear to a great extent while the resulting signal relating to physiological information merely will undergo some amplitude loss or change that can even be corrected for.

In this context, referring to FIG. 1, a device for extracting information is illustrated and denoted by a reference numeral 10. The device 10 can be utilized for recording image frames representing an object 11. The image frames can be derived from electromagnetic radiation 14 emitted or reflected by the object 11. The object 11 can be a human being or animal, or, in general, a living being. For extracting information from the recorded data, e.g. a sequence of image frames, a defined part or portion of the object 11 can be detected by a sensor means 16. The sensor means 16 can be embodied, by way of example, by a camera adapted to capture information belonging to at least a spectral component of the electromagnetic radiation 14. It goes without saying that the device 10 also can be adapted to process input signals, namely an input data stream, already recorded in advance and, in the meantime, stored or buffered. As indicated above, the electromagnetic radiation 14 can contain a continuous or discrete characteristic signal 13 which can be highly indicative of at least one at least partially periodic vital signal 12. In FIG. 1 the vital signal 12 may allow several conclusions concerning heart rate, heart rate variability, or even respiratory rate.

Existing methods for obtaining such vital signals may comprise tactile heart rate monitoring or electrocardiography, for instance. To this end, however, obtrusive monitoring was required. As indicated above, an alternate approach is directed to unobtrusive remote measuring utilizing image processing methods.

The continuous or discrete characteristic signal 13 can be delivered from the sensor means 16 to an interface 18. Needless to say, also a buffer means could be interposed between the sensor means 16 and the interface 18. Downstream of the interface 18 an extractor means 20 is provided which is adapted to extract the desired physiological information (still embedded in the characteristic index elements) from the continuous or discrete characteristic signal 13. Further, a converter means 22 may follow which is adapted for processing the physiological information derived by the extractor means 20. The preprocessed signal extracted by the extractor means 20 still can comprise large noise-indicative components. In this connection, the converter means 22 can be applied for isolating and enhancing the desired signal component indicative of the vital signal 12 of interest from the overall signal delivered thereto.

Having extracted an enhanced signal component further post processing of data can be carried out by an analyzing means 24. To this end, the post processing can comprise bandwidth filtering and/or Fourier analysis. Further post processing measures can be envisaged contributing to an even further improved detection of the desired signal of interest, e.g. of a dominant heart beat indicative frequency peak in the continuous or discrete characteristic signal 13.

The extractor means 20, the converter means 22, and the analyzing means 24 can be jointly embodied by a common processing unit 26, e.g. a central processing unit having a single processor or multiple processors. Also the interface 18 can be connected thereto in a common processing device 28 housing the respective subcomponents. By way of example, the processing device 28 can be embodied by a personal computer driven by respective logic commands. In case the sensor means 16 is also jointly connected to the interface 18 by means of hardware, a capturing unit 30 may house the respective subcomponents.

However, in the alternative, it can be envisaged to combine a separate sensor means 16 with the processing device 28. This connection can be established by means of cable links or by means of wireless links. In place of the sensor means 16 also a storage means comprising prerecorded data could be connected to the processing device 28.

Figure 2:
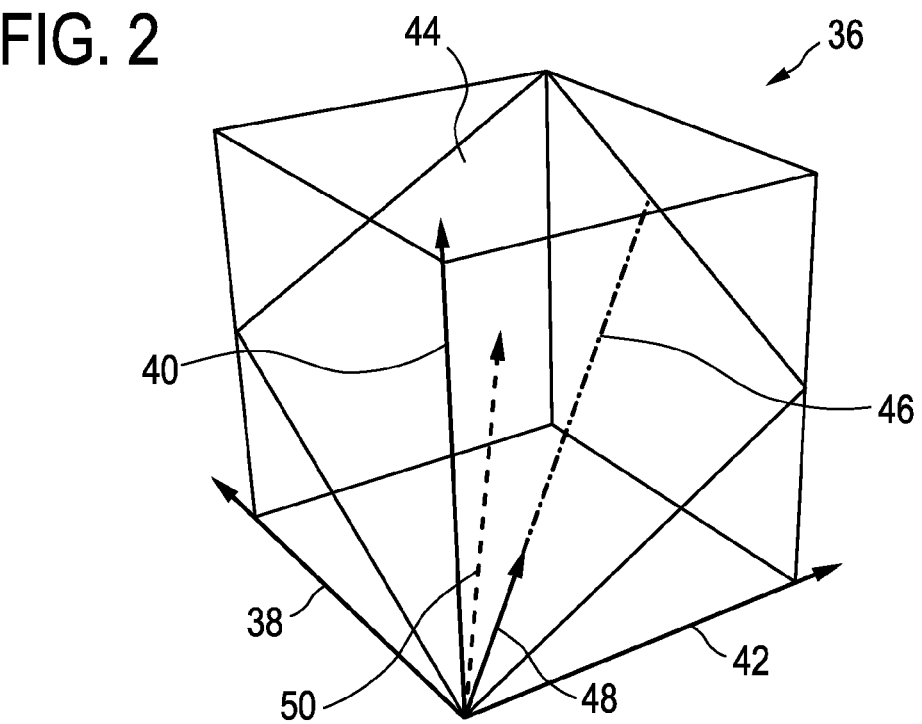
FIG. 2 shows a sample schematic illustration of a signal space to which a normalization can be applied.

As indicated above, the extractor means 20 can be further adapted to carry out some preprocessing of the received data so as to already enhance the signal-to-noise ratio in preparation for subsequent analyses addressed to the desired vital signals. A possible preprocessing step may be a luminance normalization resulting in a signal space somehow simplified in view of the number of represented dimensions, or, so to say, the number of spectral components or spectral variety. By way of example, the resulting signal space can be referred to as a chromaticity plane. In this connection, FIG. 2 depicts a sample signal space 36 to which a luminance normalization is applied. The basic signal space 36 is indicative of three main spectral components 38, 40 and 42, e.g., when the RGB space is utilized, a red, green and blue component of the visible spectrum.

It should be understood that, when the signal of interest is a signal varying over time, i.e., in the end, the at least one at least partially periodic vital signal 12, difference values rather than absolute values are to be considered for assessing vital information embedded in the captured signals. By way of example, when aiming at an extraction of the heart rate or suchlike from visible radiation reflected by the object 11, a plurality of characteristic index elements 50 associated with a color space, i.e. the signal space 36, can be drawn from the captured signals, i.e. the image sequence. Each of the characteristic index elements 50 can represent an 'actual' difference value, as mainly the signal components varying due to the variation of the at least one at least partially periodic vital signal 12 are of interest. To this end, each of the characteristic index elements 50 can represent a color change in the color space determined between two distinct of even successive points in time; in this regard, also refer to Equation (6).

Thus, it should be noted that, in principle, the signal space 36 may also comprise further quadrants or half-spaces indicative of negative values of the spectral components 38, 40 and 42. As difference values are represented in the signal space 36 also negative values can occur. Needless to say, when difference values are considered, each of the plurality of characteristic index elements 50 originates from the point of origin, also refer to FIG. 5. By applying a luminance normalization (ref Equation (7)) a subspace can be determined in the signal space 36. In FIG. 2 the chromaticity plane or normalized signal space is indicated by a reference numeral 44. By means of the luminance normalization the respective signal components can be transferred to the chromaticity plane or normalized signal space 44, thereby enabling a simplified analysis thereof.

Figure 3:
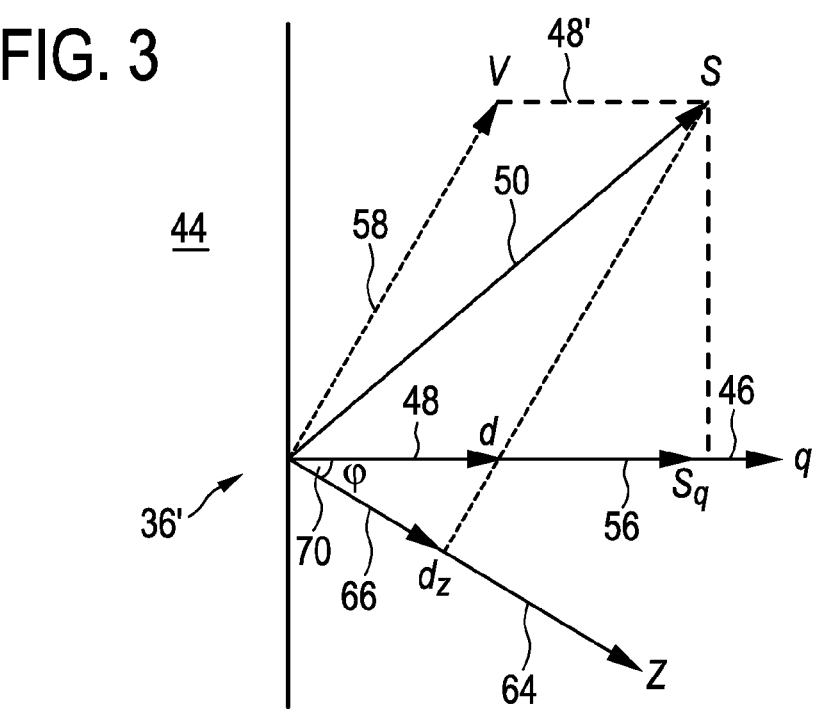
FIG. 3 shows a sample schematic illustration of a normalized signal space in which a predetermined index element and a disturbance-reduced index element are illustrated.
Figure 4:
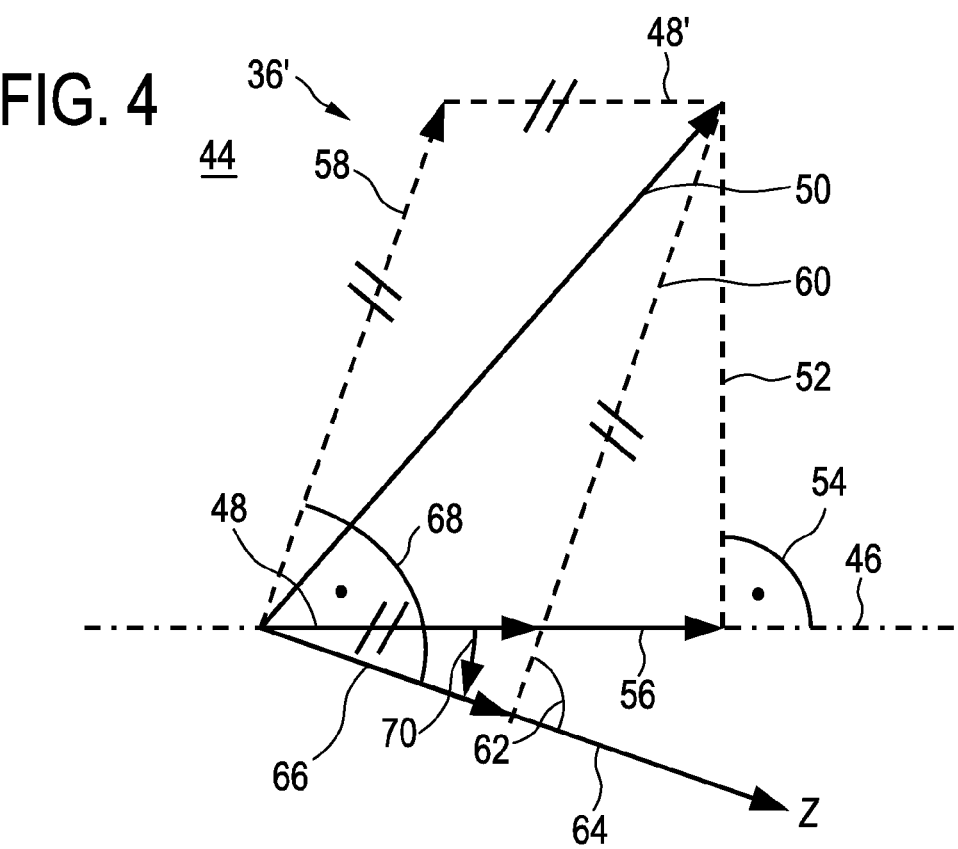
FIG. 4 shows a further schematic illustration of a normalized signal space comparable with the signal space of FIG. 3.
Figure 5:
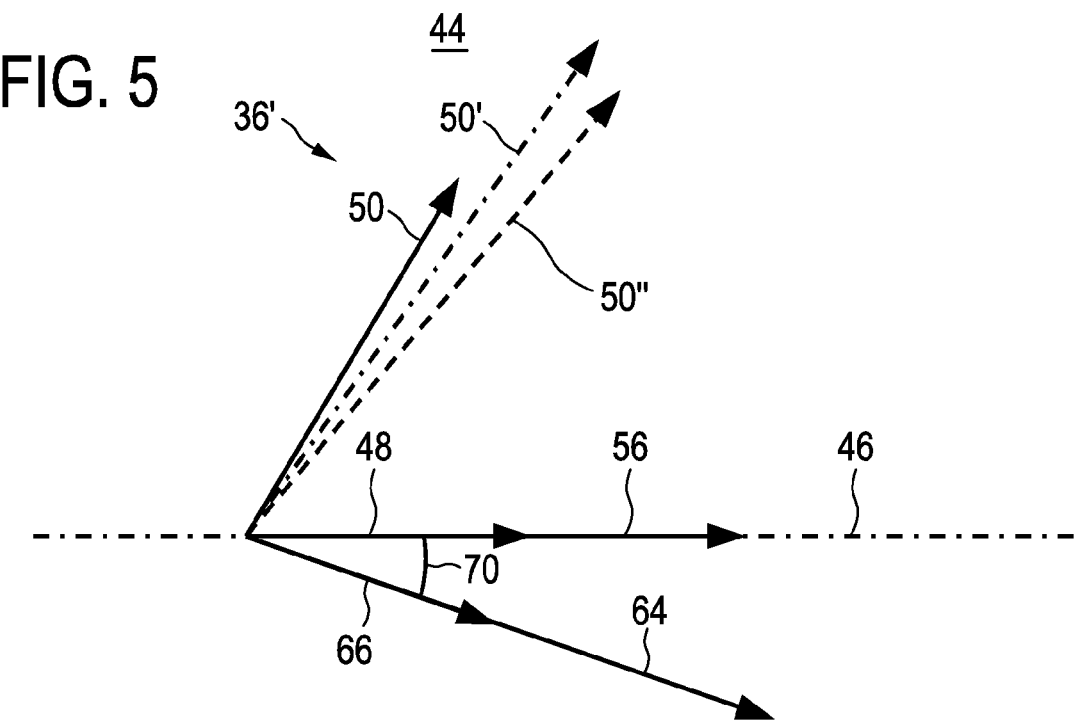
FIG. 5 shows an even further schematic illustration of a signal space wherein a plurality of characteristic index elements is illustrated.

Further referring to FIG. 3, FIG. 4 and FIG. 5 wherein the chromaticity plane or normalized signal space 44 is illustrated more detailed in plan view, it can be understood that the dimensionality of the problem underlying the desired extraction of vital signals from the captured data can be reduced by the normalization measures. In other words, referring again to the fact that each of the characteristic index elements 50 can be considered a vector quantity, the number of vector row values required for specifying the vectors can be reduced to a great extent.

FIG. 2 further displays a predetermined index element 46 which can be considered, for instance, a so-called heart beat axis which is assumed to represent a set orientation of the expected vital signal in the signal space 36. Preferably, also the predetermined index element 46 is transferred to the chromaticity plane or normalized signal space 44. As indicated above, it can be envisaged to project the characteristic index element 50 to the predetermined index element 46, thereby arriving at a signal component 56, ref. FIG. 3 and FIG. 4. However, this component, also referred to as noise-containing signal 56, still comprises components indicative of noise in that the projection applied to the characteristic index element 50 merely eliminates noise that is orthogonal to the predetermined index element 46. Further, the physiological information which is highly representative of the at least one at least partially periodic vital signal 12 is denoted by reference numeral 48. The physiological information 48 is assumed to coincide with the predetermined index element 46.

According to the approach outlined above, it would be further advantageous to define a further index element, the so-called disturbance-reduced index element 64, having an orientation derived from the main orientation of the disturbing noise components overlaying the desired signals in the data stream.

However, the determination of this desired line or axis provides a further challenge. Basically, the characteristic index elements 50 could be projected to the predetermined index element 46 or to further alternative elements, e.g. any desired axis in the signal space 36. When applying a projection to alternative elements deviating from the predetermined index element 46, some amplitude loss of the signal of interest, the physiological information 48, has to be expected. However, as mentioned above, the loss of amplitude can be corrected for by applying a conversion factor considering the different orientation of both elements.

FIG. 3, FIG. 4 and FIG. 5 illustrate the proposed approach to the drawback outlined above. Each figure depicts a normalized signal space 36' embodied by the chromaticity plane or normalized signal space 44. Referring to FIG. 3 a sample embodiment, namely the detection of heart rate signals in image frames is exemplified. A vector d corresponds to a color difference vector only induced by the heartbeat, or, so to say, to the desired physiological information 48. A vector v corresponds to a color difference due to the distortion or noise; the vector v also can be referred to as a disturbing signal component which is denoted by a reference numeral 56. A vector s corresponds to the captured and extracted characteristic index element 50 which can be considered a composition of the vectors d and v or, respectively, the disturbing signal component 56 and the desired physiological information 48. In FIG. 3 it is assumed that the distortion is somehow augmented to the desired signal. Needless to say, in principle, any linear combination of vectors in the normalized signal space 36' could be presumed. Further, a vector q corresponds to the so-called heart beat axis, namely the predetermined index element 46 which can be empirically determined, at least approximately. When simply projecting the measured vector on the so-called heart beat axis q, a vector $s_q$ can be obtained which corresponds to the noise-containing signal 56 which still contains noise components orientated parallel to the heart beat axis q.

In other words, the vector sq, the noise-containing signal 56, still contains a part of an undesired distortion vector v. The distortion vector v corresponds to the so-called disturbing signal component 58 which is generally unknown and, hence, cannot be utilized for an immediate derivation of the desired physiological information 48 therefrom. The characteristic index element 50 can be considered a linear combination of the disturbing signal component 58 and the desired physiological information 48; in this regard, it is also referred to a parallel translation denoted by 48'. In the initial state, however, merely the orientation and length of the characterized index element 50 and the overall orientation of the predetermined index element 46 enabling an approximate understanding of the general orientation of the physiological information 48 are known.

In contrast, when, however, a projection to the fairly unknown vector z which is supposed to be approximately orthogonal to the distortion vector v could be applied to the vector s, a vector $d_z$ could be obtained. The vector z corresponds to a so-called disturbance-reduced index element denoted by a reference numeral 64 while vector $d_z$ corresponds to a projected index element denoted by a reference numeral 66. Basically, the vector $d_z$ does not contain noise-containing components worth mentioning. The length of the vector $d_z$ is proportional to the length of the heart beat difference vector d and therefore highly indicative of the desired vital signal. The vector z can be considered a 'dynamic' heart beat axis the orientation of which varies over time according to the variations of the vector v, namely the disturbing signal component 58.

The determination of the vector z, the disturbance-reduced index element 64, establishes a major challenge as the orientation of the vector v to which the vector z should be orthogonal is fairly unknown. To this end, statistical methods can be utilized for analyzing a plurality of vectors s derived from a sequence captured over time, the so-called plurality of characteristic index elements 50. Such a plurality of characteristic index elements is illustrated in FIG. 5 and denoted by reference numerals 50, 50' and 50".

For the sake of completeness, again referring to FIG. 3 and FIG. 4, further elements are presented. A projection line indicting the projection of the characteristic index element 50 to the predetermined index element 46 leading to the signal component 56 is denoted by reference numeral 52. It goes without saying, that the predetermined index element 46 and the projection line 52 form a right angle 54.

Basically, the same applies to the projection line 60 indicating the projection of the characteristic index element 50 to the disturbance-reduced index element 64 both of which forming a basically right angle 62. The projection line 60 is basically parallel to the disturbing signal component 58. Therefore, also the disturbing signal component 58 and the disturbance-reduced index element 64 form a basically right angle 68. However, as presented in the following, in case a 'merely' an approximate determination of the disturbance-reduced index element 64 can be carried out which may be even based on a plurality of characteristic index elements probably having a different length and orientation, it should be noted that the angle 68 can be considered a merely approximately right angle 68.

In case the signal space 36 is a normalized signal space 36' represented by a two-dimensional 'difference' color space, at least two characteristic index elements 50 are required for an approximate determination of the disturbance-reduced index element 64. When, however, the signal space 36 is represented by a three-dimensional 'difference' color space, at least three characteristic index elements 50 are required. As each of the characteristic index elements 50 may be different from its precursor and/or its successor due to variations of the overall signal, the proposed approach cannot be directed to determine a disturbance-reduced index element 64 which is exactly orthogonal to each of the extracted characterized index elements 50 at the same time.

In contrast, assuming that the disturbing signal components 58 are considerably large compared to the desired physiological information 48, it can be envisaged to determine the disturbance-reduced index element 64 in a way so as to obtain a 'reference axis' which is at least to some extent correlated with the predetermined index element 46. Further, the determination can be further directed to minimize the energy of the characteristic index elements 50 when projected on the disturbance-reduced index element 64, namely the projected index elements 66.

In doing so, the influence of the distortion in the obtained projected index element 66 is clearly limited. However, since the determined disturbance-reduced index element 64 is correlated with the 'original' predetermined index element 46, the obtained signal derivable from the pulsation of the projected index elements 66 over time is still highly indicative of the desired vital signal, e.g. the heart rate. Again, needless to say that the obtained projected index elements 66 can be scaled in case the vector z they are projected to does not coincide with the 'original' vector q, i.e. the predetermined index element 46. In this connection, it should be noted that, in case the disturbance-reduced index element 64, cf. the vector z, varies over time, it is preferred if also time-variant scale factors are to be applied.

In the following sample derivations of the desired elements are depicted in terms of mathematical symbols rather than reference numerals, which were also used in the above to denote respective elements. However, for the sake of visualization, also FIG. 3, FIG. 4 and FIG. 5 can be referred to, wherein FIG. 3 provides some 'translation' of the elements.

By way of example, it can be envisaged to stack a plurality, denoted by N, difference row vectors $s^T$, cf. the characteristic index elements 50, into an N×2 matrix S, when referring to the two-dimensional case. In order to find the vector z with, by way of example, a length one that minimizes the energy of the projected difference vectors Sz, the expression $\|Sz\|^2 = (Sz)^T Sz = z^T(S^T S)z$ can be considered.

Throughout this document, the (Euclidean) length of a vector $x \in \mathbb{R}^N$, $x=[x_0, \ldots, x_{N-1}]^T$ where $^T$ denotes transposition can be denoted by $$\|x\| = \sqrt{\langle x,x \rangle} = \sqrt{x^T x} = \sqrt{x_0^2 + x_1^2 + \ldots + x_{N-1}^2}.$$

The vector z that minimizes the expression provided above can be determined by methods of multivariate statistics, such as, by way of example, by utilizing principle component analysis. Eventually the vector z which can be supposed to be chosen equals an eigenvector of the matrix $s^T s$ which is associated with the smallest eigenvalue. In case the detected vector z is not orthogonal to the heart beat axis q, a solution is achieved. Otherwise, in a stepwise process, the eigenvector of $s^T s$ associated with the next smallest eigenvalue can be considered, and so forth.

This approach may be further improved by applying a threshold to the detected eigenvalue as to detect solutions wherein the detected vector z is close to orthogonal to the heart beat axis q. In this connection, the refinement addresses a possible drawback that might lead to a considerably large scale factor to be applied to the vector d, in case a correction for the loss of amplitude related thereto is desired. In general, the scale factor can be equal to $\langle z, q \rangle^{-1}$, which directly follows from $\langle z,q \rangle = \|z\|\|q\| \cos \phi = \cos \phi$. Basically, a remedy would be to apply the threshold. In case the actual eigenvalue is smaller than this threshold, the respective eigenvector can be discarded and the remaining eigenvectors are to be considered.

However, it would be further advantageous to avoid the threshold. In fact, when considering, by way of example, a two-dimensional case, the eigenvector close to orthogonal to the heart beat axis q can be considered the optimal value, if the distortions are very small, or if the distortions are mainly orientated along the heart beat axis q. In that case, a vector highly correlated with the heart beat axis q can be considered a good choice, since a differentiation between the desired signal, e.g. the heartbeat, and the noise-containing distortion components v on the heart beat axis q is difficult.

A further challenge could derive from the fact that the presented eigenvector approach most likely does not provide a closed-form solution. The optimal vector z is selected from a collection of eigenvectors depending on the associated eigenvalues and the correlation with the heart beat axis q.

An alternative approach for the detection of the optimal vector z, denoted by 2 throughout this document, will be proposed in the following. As indicated above, it would be preferred if a closed-form solution could be detected which, further preferred, comprised the tendency to highly correlate with the heart beat axis q.

Basically, such a solution could be achieved by applying a weight function $\langle z,q \rangle^{-1}$ to the projected differences Sz. This weight function can be defined in a way as to become large when the vector z approaches an orientation fairly orthogonal to the heart beat axis q. Eventually, a solution can be achieved being provided with the tendency to keep away from this state. It goes without saying that other weight functions that look similar can be used. By way of example, the weight functions $1+x(1-\langle z,q \rangle^2)/\langle z,q \rangle$ and $\pi^2/(\pi^2-4c \arccos^2\langle z,q \rangle)$ with c a positive constant can be used as well. To sum it up, it would be desirable to find the vector z with length one that minimizes $\|\langle z,q \rangle^{-1} Sz\|^2$.

In the following, it will be demonstrated in detail that the resulting minimum has a closed-form solution that basically reads $\hat{z}=\|(S^T S)^{-1}(S^T S)^{-1} q$. The respective sample derivations relate to the two-dimensional and three-dimensional case. Again, it should be noted that, e.g. when considering luminance normalization or similar preprocessing, the signal space to which the analysis is applied may comprise two, three, or even further dimensions. A further assumption can be made in that the inverse of the matrix $S^T S$ always exists. This condition is fulfilled as long as the difference vectors s of interest span the complete signal space under consideration, i.e. the vectors also comprise components in two, three, or even further dimensions. By utilizing this approach, an optimal vector 2 can be determined which does not significantly deviate from the optimal vector found by the eigenvector approach if the angle between this vector z and the heart beat axis q remains considerably small. In this event the weight function would be close to one leading to the term $\|\langle z,q \rangle^{-1} Sz\|^2 \approx \|Sz\|^2$.

However, deviation between the two approaches can be expected when the mentioned angle, cf. the angle $\phi$ in FIG. 3 denoted by a reference numeral 70, becomes larger, in particular when it approaches 90° (degrees). In that case also the optimal vector $\hat{z}$ determined by applying the proposed approach becomes orthogonal to the heart beat vector q. Nevertheless, in practice, this is very unlikely to happen, since always some distortion has to be expected.

In a further advanced embodiment, it can be envisaged that, by applying Parseval's energy theorem, the optimization can be refined in a Fourier domain. In this way, desired frequency bands that are highly indicative of the vital signal of interest can be selected during the optimization.

According to an event further refinement a band pass filtering can be applied to the obtained signal form. To this end, preferably, the frequency bands corresponding to the heart beat range are selected or, at least, enhanced. By way of example, the frequency range of interest can comprise a range from 40 BPM (beats per minute) to 210 BPM. In this way, the optimal vector $\hat{z}$ is not influenced by noise outside this range of interest.

According to an embodiment, a two-dimensional solution is derived in the following. In the two-dimensional case, the optimal vector $\hat{z}$ basically reads $$\hat{z} = \arg\min_{z \in \mathbb{R}^2, \|z\|=1} \left\| \frac{Sz}{\langle z, q \rangle} \right\|^2.$$

wherein the vector q, considering $\|q\|=1$, corresponds to the (empirically found) heart beat axis q. Further, the N×2 matrix S comprises rows corresponding to mean differences (e.g. embodied by a plurality of vectors v) in the signal space, e.g. the chromaticity plane.

The equation can be rewritten in matrix form:

$$\left\| \frac{Sz}{\langle z, q \rangle} \right\|^2 = \frac{z^T S^T S z}{\langle z, q \rangle^2}.$$

In this equation, the matrix $S^T S$ can be considered a symmetric positive (semi)definite matrix, and can be expressed as $S^T S = E D E^T$, wherein the columns of the matrix E correspond to the eigenvectors, and the diagonal elements of the diagonal matrix D correspond to the eigenvalues of the matrix $S^T S$:

$$\frac{z^T S^T S z}{\langle z, q \rangle^2} = \frac{z^T E D E^T z}{\langle z, q \rangle^2}.$$

By using the unitary property of the matrix E, i.e. $E^{-1}=E^T$, the following can be noted:

$$\frac{z^T E D E^T z}{\langle z, q \rangle^2} = \frac{z^T E D E^T z}{\langle E^T z, E^T q \rangle^2}.$$

Further, substitutions $y=E^T z$ and $v=E^T q$ can be applied that yield an intermediate result that reads $$\left\| \frac{Sy}{\langle Ey, q \rangle} \right\|^2 = \frac{y^T D y}{\langle y, v \rangle^2}. \tag{8}$$

It should be noted that $\|y\|=\|E^T z\|=\|z\|=1$ and $\|v\|=\|E^T q\|=\|q\|=1$, since the matrix E is unitary. For convenience, the following notation can be used $$y = E^T z = \begin{bmatrix} y_0 \\ y_1 \end{bmatrix}, D = \begin{bmatrix} \lambda_0 & 0 \\ 0 & \lambda_1 \end{bmatrix}, v = E^T q = \begin{bmatrix} v_0 \\ v_1 \end{bmatrix}, \tag{9}$$

wherein $\lambda_0$ and $\lambda_1$ are the eigenvalues of the matrix $S^T S$. Further looking for a solution of the vector y on the unit circle the vector y can be therefore written in terms of polar coordinates, i.e. $y_0 = \cos\phi$ and $y_1 = \sin\phi$. By using the notation (9) and polar coordinates, the intermediate result (8) in terms of the angle $\phi$ reads $$C(\varphi) = \frac{\lambda_0 \cos^2\varphi + \lambda_1 \sin^2\varphi}{(v_0\cos\varphi + v_1\sin\varphi)^2}. \qquad (10)$$

For detecting the minimum value of this expression $C(\phi)$ for a given vector v and eigenvalues $\lambda_0$ and $\lambda_1$, the first derivative of this expression with respect to the angle $\phi$ can be calculated:

$$\frac{dC(\varphi)}{d\varphi} = \frac{2v_0\lambda_1\sin\varphi - 2v_1\lambda_0\cos\varphi}{(v_0\cos\varphi + v_1\sin\varphi)^3}.$$

Setting this first derivative equal to zero, the solution follows from $$\lambda_1 v_0 \sin\phi - \lambda_0 v_1 \cos\phi = 0, \qquad (11)$$

provided that $$\langle y, v \rangle = v_0 \cos\phi + v_1 \sin\phi \neq 0.$$

It can directly follow that the angle $\phi = \phi_s$ while $\tan\phi_s = \lambda_0 v_1 / \lambda_1 v_0$ is a solution, and, as a consequence, the optimal vectors $\hat{y}$ and $\hat{z}$ read $$\hat{y} = \begin{bmatrix} \cos\varphi_s \\ \sin\varphi_s \end{bmatrix} = \frac{1}{\sqrt{\lambda_0^2 v_1^2 + \lambda_1^2 v_0^2}} \begin{bmatrix} \lambda_1 v_0 \\ \lambda_0 v_1 \end{bmatrix}, \text{ and } \hat{z} = E\hat{y}. \qquad (12)$$

It should be noted that $$\langle \hat{y}, v \rangle = v_0\cos\varphi_s + v_1\sin\varphi_s = \frac{\lambda_1 v_0^2 + \lambda_0 v_1^2}{\sqrt{\lambda_1^2 v_0^2 + \lambda_0^2 v_1^2}} \geq 0,$$

since the eigenvalues $\lambda_0 \geq 0$ and $\lambda_1 \geq 0$.

A further consideration has to be carried out in case both eigenvalues equal zero, if the eigenvalue $\lambda_0 = 0$ and $v_0 = 0$, or if the eigenvalue $\lambda_1 = 0$ and $v_1 = 0$.

Both eigenvalues equal to zero, can only be a result if the matrix S contains only zeros, or, equivalently, if all differences are zero. In practice, this most likely will never happen.

The second or the third case, is about to happen when all differences in the matrix S coincide with or are orthogonal to the heart beat axis q. In this case, the eigenvector associated with the largest eigenvalue coincides with the heart beat axis q, and the eigenvector associated with the zero eigenvalue is orthogonal to the heart beat axis q, or vice versa. For these two cases the intermediate result (10) equals a constant for all angles $\phi$, and there exists no minimum. In other words, all vectors z on the unit circle are equally correct. In this case, it is fairly unclear which vector is obtained in the limit. However, in practice, one eigenvalue which is equal to zero is not likely to happen, due to the inevitable noise in the difference vectors s.

Further consideration of the optimal vector $\hat{z}$ [see equations (9) and (12)], and using the expression of the inverse of the matrix $S^T S$ $$det(S^T S)(S^T S)^{-1} = det(EDE^T)ED^{-1}E^T = det(D)ED^{-1}E^T = E\hat{D}E^T,$$

with $$\hat{D} = det(D)D^{-1} = \begin{bmatrix} \lambda_1 & 0 \\ 0 & \lambda_0 \end{bmatrix},$$

reveals that $$\hat{z} = E\hat{y} = \frac{1}{\sqrt{\lambda_0^2 v_1^2 + \lambda_1^2 v_0^2}} E\hat{D}E^T q = \frac{(S^T S)^{-1} q}{\|(S^T S)^{-1} q\|},$$

provided that all eigenvalues are larger than zero, i.e. the inverse of the matrix $S^T S$ exists. As a consequence, the optimal vector $\hat{z}$ can be computed without the computation of the eigenvectors and eigenvalues of the matrix $S^T S$.

Noted that $$\langle q, \hat{z} \rangle = \frac{q^T (S^T S)^{-1} q}{\|(S^T S)^{-1} q\|} \geq 0$$

for all possible heart beat axes q, since $(S^T S)^{-1}$ is a positive definite matrix. Or, in other words, the vector $\hat{z}$ is always directed in the positive direction of the heart beat axis q. Moreover, the minimum for the optimal vector $\hat{z}$ equals $$\left\| \frac{S\hat{z}}{\langle \hat{z}, q \rangle} \right\|^2 = \frac{1}{q^T (S^T S)^{-1} q}.$$

And finally, by using Parseval's energy theorem arriving at $$\left\| \frac{Sz}{\langle z, q \rangle} \right\|^2 = \left\| \frac{FSz}{\langle z, q \rangle} \right\|^2,$$

with F the unitary N×N Fourier matrix, i.e. $F^{-1} = F^*$. Or, in other words, optimizing in the Fourier domain yields the same optimal vector $\hat{z}$.

This observation leads to an optimization refinement in that the frequency bins of the Fourier transformed columns of the matrix FS can be selected in the range of interest, e.g. the frequency bins corresponding to the heart beat range from, by way of example, 40 BPM to 210 BPM. In this way, the optimum is not influenced by the noise in the frequency bins outside the range of interest.

Or, expressed more formally, the matrix FS can be multiplied with an N×N selection matrix R which is a diagonal matrix with zeros and ones on the diagonal in order to arrive at the optimal vector $\check{z}$:

$$\check{z} = \arg \min_{z \in \mathbb{R}^2, \|z\|=1} \left\| \frac{RFSz}{\langle z, q \rangle} \right\|^2 = \arg \min_{z \in \mathbb{R}^2, \|z\|=1} \left\| \frac{\tilde{S}z}{\langle z, q \rangle} \right\|^2$$

with $\tilde{S} = RFS$.

Eventually the optimal vector becomes $$\check{z} = \frac{(\tilde{S}^*\tilde{S})^{-1}q}{\|(\tilde{S}^*\tilde{S})^{-1}q\|},$$

where S* corresponds to the Hermitian transposed matrix S. This expression should be emphasized and can be considered a preferred elegant embodiment which is, moreover, fairly simple to implement to the device or the method of the invention.

According to an alternative embodiment, in the following a three-dimensional solution is derived. In the three-dimensional case, the optimal vector 2 of interest reads $$\hat{z} = \arg\min_{z \in \mathbb{R}^3, \|z\|=1} \left\|\frac{Sz}{\langle z, q\rangle}\right\|^2,$$

wherein the vector q, with $\|q\|=1$, and the N×3 matrix S the rows of which correspond to the mean differences in the signal space, e.g. in a RGB color space or even in a logarithmic log RGB domain.

The derivation of the intermediate result is similar to the derivation of the intermediate result in the two-dimensional case [see Equation (8)]:

$$\left\|\frac{SEy}{\langle Ey, q\rangle}\right\|^2 = \frac{y^T D y}{\langle y, v\rangle^2}. \tag{13}$$

However, in the three-dimensional case, the columns of the matrix E contain the three eigenvectors, and the diagonal elements of the diagonal matrix D correspond to the three eigenvalues of the 3×3 matrix $S^T S$.

Now the following notation is utilized [cf. Equation (9)]

$$y = E^T z = \begin{bmatrix} y_0 \\ y_1 \\ y_2 \end{bmatrix}, D = \begin{bmatrix} \lambda_0 & 0 & 0 \\ 0 & \lambda_1 & 0 \\ 0 & 0 & \lambda_2 \end{bmatrix}, v = E^T q = \begin{bmatrix} v_0 \\ v_1 \\ v_2 \end{bmatrix}, \tag{14}$$

wherein $\lambda_0$, $\lambda_1$ and $\lambda_2$ represent the eigenvalues of the matrix $S^T S$. Also in this case, polar coordinates, especially spherical polar coordinates, of the vector y can be considered, i.e. $y_0 = \cos\theta \sin\varphi$, $y_1 = \sin\theta \sin\varphi$ and $y_2 = \cos\varphi$. The intermediate result (13) can be expressed in terms of these polar coordinates $$C(\varphi, \theta) = \frac{\lambda_0 \cos^2\theta \sin^2\varphi + \lambda_1 \sin^2\theta \sin^2\varphi + \lambda_2 \cos^2\varphi}{(v_0 \cos\theta\sin\varphi + v_1 \sin\theta\sin\varphi + v_2 \cos\varphi)^2}.$$

Further, to determine the minimum of this expression, the first derivatives with respect to the angles $\varphi$ and $\theta$ can be calculated $$\frac{dC(\varphi, \theta)}{d\varphi} = \frac{c_{0,\theta}\sin\varphi - c_{1,\theta}\cos\varphi}{(v_0\cos\theta\sin\varphi + v_1\sin\theta\sin\varphi + v_2\cos\varphi)^3},$$

wherein $$c_{0,\theta} = v_2(\lambda_0 + \lambda_1 + (\lambda_0 - \lambda_1)\cos 2\theta), \text{ and} \tag{15}$$
$$c_{1,\theta} = 2\lambda_2(v_0\cos\theta + v_1\sin\theta),$$

and $$\frac{dC(\varphi, \theta)}{d\theta} = \frac{d_{0,\varphi}\cos\theta + d_{1,\varphi}\sin\theta + d_{2,\varphi}\sin\theta\cos\theta}{(v_0\cos\theta\sin\varphi + v_1\sin\theta\sin\varphi + v_2\cos\varphi)^3}, \tag{16}$$

wherein
$$d_{0,\varphi} = -2v_1(\lambda_2\cos^2\varphi + \lambda_0\sin^2\varphi)\sin\varphi,$$
$$d_{1,\varphi} = 2v_0(\lambda_2\cos^2\varphi + \lambda_1\sin^2\varphi)\sin\varphi,$$
and
$$d_{2,\varphi} = -2v_2(\lambda_0 - \lambda_1)\cos\varphi\sin^2\varphi.$$

In the first instance, the derivative with respect to $\varphi$ can be considered in more detail. Setting this first derivative equal to zero, the solution follows from $$c_{0,\theta}\sin\varphi - c_{1,\theta}\cos\varphi = 0,$$

provided that $$\langle y, v\rangle = v_0 \cos\theta\sin\varphi + v_1 \sin\theta\sin\varphi + v_2 \cos\varphi \neq 0.$$

It directly follows that the angle $\varphi = \varphi_s$ with $\tan\varphi_s = c_{1,\theta}/c_{0,\theta}$ is a solution. Substituting this solution $\varphi = \varphi_s$ into the first derivative with respect to $\theta$ [see Equation (16)] and by using $$\cos\varphi = \frac{c_{0,\theta}}{\sqrt{c_{0,\theta}^2 + c_{1,\theta}^2}}, \text{ and } \sin\varphi = \frac{c_{1,\theta}}{\sqrt{c_{0,\theta}^2 + c_{1,\theta}^2}}, \tag{17}$$

the following equation can be obtained $$-2v_1 c_{1,\theta}(\lambda_2 c_{0,\theta}^2 + \lambda_0 c_{1,\theta}^2)\cos\theta + 2v_0 c_{1,\theta}(\lambda_2 c_{0,\theta}^2 + \lambda_1 c_{1,\theta}^2)\sin\theta - 2v_2 c_{0,\theta} c_{1,\theta}^2(\lambda_0 - \lambda_1)\sin\theta\cos\theta = 0.$$

Dividing by $-2 c_{1,\theta}$ and further assuming that $c_{1,\theta} \neq 0$ it follows that $$v_1(\lambda_2 c_{0,\theta}^2 + \lambda_0 c_{1,\theta}^2)\cos\theta - v_0(\lambda_2 c_{0,\theta}^2 + \lambda_1 c_{1,\theta}^2)\sin\theta + v_2 c_{0,\theta} c_{1,\theta}(\lambda_0 - \lambda_1)\sin\theta\cos\theta = 0.$$

Substituting the values for $c_{0,\theta}$ and $c_{1,\theta}$ [see Equation (15)] and rearranging the expression yield $$2\lambda_2(\lambda_0 v_1 \cos\theta - \lambda_1 v_0 \sin\theta)(e_0 + e_1 \cos 2\theta + e_2 \sin 2\theta) = 0, \tag{18}$$

wherein $$e_0 = \lambda_2(v_0^2 + v_1^2) + (\lambda_0 + \lambda_1)v_2^2, \; e_1 = \lambda_2(v_0^2 - v_1^2) + (\lambda_0 - \lambda_1)v_2^2, \text{ and } e_2 = 2\lambda_3 v_0 v_1. \tag{19}$$

From Equation (18), it follows that basically two solutions can be obtained
1. $\lambda_0 v_1 \cos\theta - \lambda_1 v_0 \sin\theta = 0$;
2. $e_0 + e_1 \cos 2\theta + e_2 \sin 2\theta = 0$,
or the eigenvalue $\lambda_2 = 0$, but this case will be considered below.

The first solution can be elaborated, considering the assumptions made ($\langle y, v\rangle \neq 0$ and $c_{1,\theta} \neq 0$). Finally, it can be demonstrated that, in general, in practice, the second equation does not yield a solution with real numbers.

A solution for the first expression is $\theta = \theta_s$ with $\tan\theta_s = \lambda_0 v_1 / \lambda_1 v_0$. For this angle $\theta_s$, the following identities can be utilized $$\cos\theta_s = \frac{\lambda_1 v_0}{\sqrt{\lambda_0^2 v_1^2 + \lambda_1^2 v_0^2}}, \; \sin\theta_s = \frac{\lambda_0 v_1}{\sqrt{\lambda_0^2 v_1^2 + \lambda_1^2 v_0^2}}, \text{ and}$$

-continued $$\cos 2\theta_s = \cos^2\theta_s - \sin^2\theta_s = \frac{\lambda_1^2 v_0^2 - \lambda_0^2 v_1^2}{\lambda_1^2 v_0^2 + \lambda_0^2 v_1^2},$$

from which it follows that the coefficients $c_{0,\theta s}$ and $c_{1,\theta s}$ become [see Equation (15)]

$$c_{0,\theta_s} = \frac{2\lambda_0\lambda_1 v_2(\lambda_1 v_0^2 + \lambda_0 v_1^2)}{\lambda_1^2 v_0^2 + \lambda_0 v_1^2}, \text{ and}$$

$$c_{1,\theta_s} = \frac{2\lambda_2(\lambda_1 v_0^2 + \lambda_0 v_1^2)}{\lambda_1^2 v_0^2 + \lambda_0^2 v_1^2}.$$

Further, these expressions can be used for the coefficients $c_{0,\theta s}$ and $c_{1,\theta s}$, and by using the identities in (17), the optimal vectors $\hat{y}$ and $\hat{z}$ for the three-dimensional case can be obtained [cf. with the solution in the two-dimensional case in Equation (12)]

$$\hat{y} = \begin{bmatrix} \cos\theta_s \sin\varphi_s \\ \sin\theta_s \sin\varphi_s \\ \cos\varphi_s \end{bmatrix} = \qquad (20)$$

$$\frac{1}{\sqrt{\lambda_1^2\lambda_2^2 v_0^2 + \lambda_0^2\lambda_2^2 v_1^2 + \lambda_0^2\lambda_1^2 v_2^2}} \begin{bmatrix} \lambda_1\lambda_2 v_0 \\ \lambda_0\lambda_2 v_1 \\ \lambda_0\lambda_1 v_2 \end{bmatrix} = \frac{\hat{D}v}{\|\hat{D}v\|} \text{ and}$$

$$\hat{z} = E\hat{y},$$

wherein $\hat{D} = \det(D)D^{-1}$. Also in this case $$\langle y, v \rangle = v_0 \cos\theta\sin\varphi + v_1 \sin\theta\sin\varphi + v_2\cos\varphi = \frac{\lambda_1\lambda_2 v_0^2 + \lambda_0\lambda_2 v_1^2 + \lambda_0\lambda_1 v_2^2}{\lambda_1^2\lambda_2^2 v_0^2 + \lambda_0^2\lambda_2^2 v_1^2 + \lambda_0^2\lambda_1^2 v_2^2} \geq 0$$

applies, since the eigenvalues $\lambda_0 \geq 0$, $\lambda_1 \geq 0$ and $\lambda_2 \geq 0$.

In this connection, problems can be expected when all the eigenvalues are zero, when $\lambda_0 = v_0 = 0$, $\lambda_1 = v_1 = 0$, or when $\lambda_2 = v_2 = 0$. However, this is unlikely to occur in practice.

Further, it will be demonstrated that the second equation $e_o + e_1 \cos 2\theta + e_2 \sin 2\theta = 0$ does not yield a solution with real numbers in practice. Rewriting this expression in $$e_0 \cos 2\theta + e_2 \sin 2\theta = e_0 + \sqrt{e_1^2 + e_2^2}\sin(2\theta + \arctan 2(e_1, e_2))$$

wherein arctan 2 corresponds to the four quadrant inverse tangent, directly yields the solution $$\hat{\theta}_s = -\frac{1}{2}\arcsin\left(\frac{e_0}{\sqrt{e_1^2 + e_2^2}}\right) - \frac{1}{2}\arctan 2(e_1, e_2) + k\pi,$$

wherein k is an integer. However, if $|e_0/\sqrt{e_1^2+e_2^2}|>1$, or equivalently, if $e_1^2+e_2^2-e_0^2<0$, then this results in a solution with a complex angle. Using the expressions for $e_0$, $e_1$ and $e_2$ in (12), we arrive at $$e_1^2 + e_2^2 - e_0^2 = -4v_2^2(\lambda_1\lambda_2 v_0^2 + \lambda_0\lambda_2 v_1^2 + \lambda_0\lambda_1 v_2^2)$$

which is always smaller than zero, except for when at least two eigenvalues are zero, or when $v_2=0$. However, as stated above, at least two eigenvalues equal to zero is unlikely to happen.

The second case, $v_2=0$, cannot occur. The equality $v_2=0$ means that $\langle E_2, E^T q \rangle = 0$, wherein $E_2$ corresponds to the eigenvector in the third column of the matrix E, or equivalently, $\langle EE_2, q \rangle$. However, this expression is equal to $q_2 \neq 0$. Thus, if a heart beat component $q_2$ in the direction of the luminance changes exists, $v_2=0$ never occurs.

And finally, similar to the two-dimensional case, a closed-form solution for the optimal vector $\hat{z}$ reads $$\hat{z} = \frac{(S^T S)^{-1} q}{\|(S^T S)^{-1} q\|},$$

Wherein the optimal vector $\hat{z}$ is always directed in the positive direction of the heart beat axis q $$\langle q, \hat{z} \rangle = \frac{q^T (S^T S)^{-1} q}{\|(S^T S)^{-1} q\|} \geq 0,$$

and wherein the minimum for the optimal vector $\hat{z}$ equals $$\left\|\frac{S\hat{z}}{\langle \hat{z}, q \rangle}\right\|^2 = \frac{1}{q^T (S^T S)^{-1} q}.$$

Finally, the optimal vector z obtained after a frequency bins selection becomes $$\check{z} = \frac{(\tilde{S}^* \tilde{S})^{-1} q}{\|(\tilde{S}^* \tilde{S})^{-1} q\|}.$$

Also this expression should be emphasized and can be considered a preferred elegant embodiment which is, moreover, fairly simple to implement to the device or the method of the invention.

Figure 6:
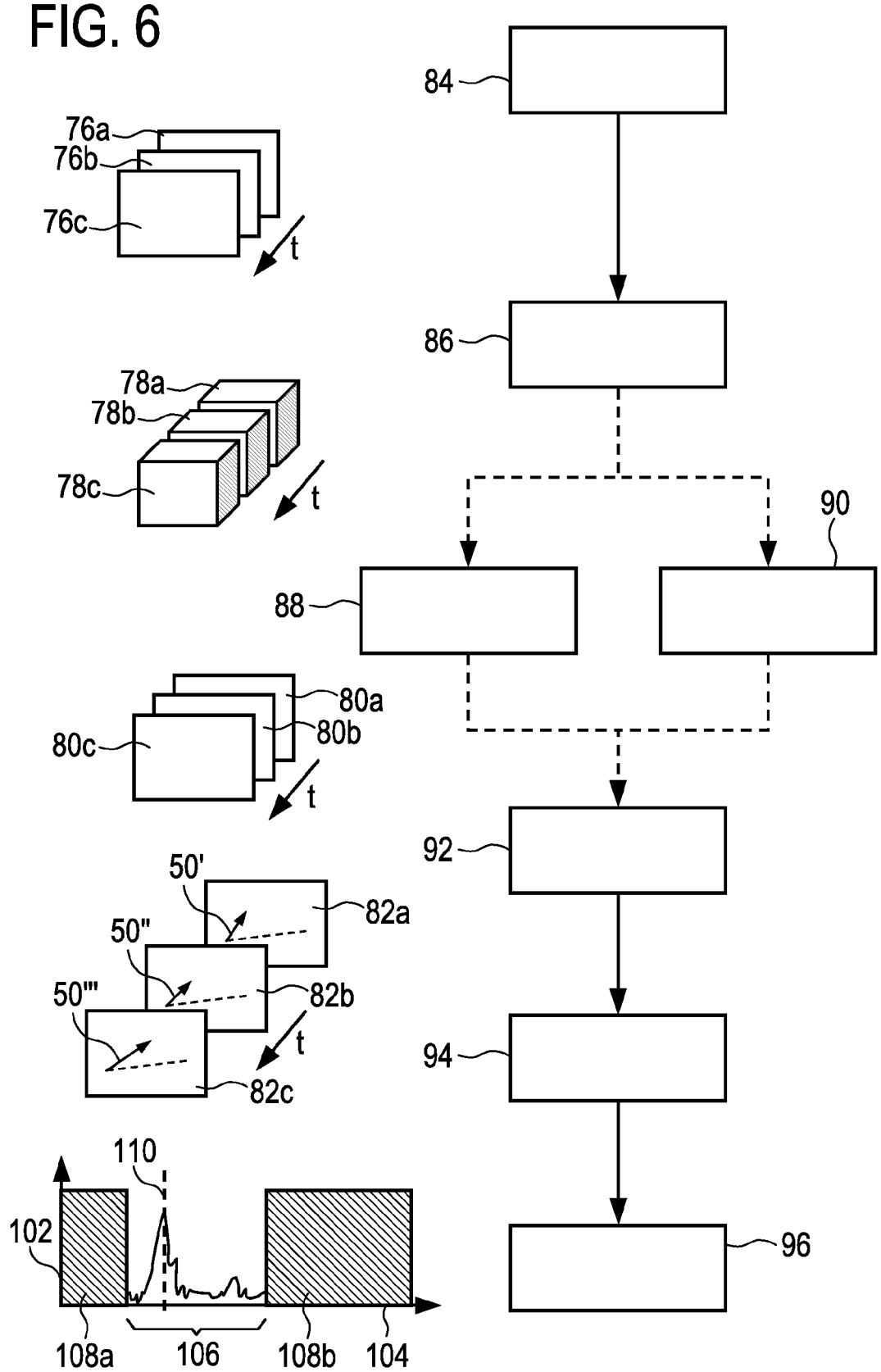
FIG. 6 shows an illustrative block diagram representing several steps of an embodiment of a method according to the invention.

Having demonstrated several alternative sample approaches covered by the invention, FIG. 6 is referred to, schematically illustrating a method for extracting information from characteristic signals.

Initially, in a step 84 an input data stream 76*a*, 76*b*, 76*c* is received. The data stream 76*a*, 76*b*, 76*c* can be delivered from a sensor means 16 or a data buffer or storage means. The data stream 76*a*, 76*b*, 76*c* can be embodied, by way of example, by a sequence of image frames varying over time t.

In a subsequent step 86 signals of interest derived from the input data stream 76*a*, 76*b*, 76*c* can be processed and transferred to signal spaces thereby creating the preprocessed data stream 78*a*, 78*b*, 78*c*. The processing related thereto can comprise the detection of an area of interest of an object from which the input data stream 76*a*, 76*b*, 76*c* is derived. Further, the step 86 may also comprise a compensation of motions of the object represented in the input data stream 76*a*, 76*b*, 76*c*. In other words, an area of interest indicative of the desired information can be tracked over time in the input data stream 76*a*, 76*b*, 76*c*.

Subsequently, a color normalization 88 and/or a luminance normalization 90 can be applied to the preprocessed data stream 78a, 78b, 78c. Consequently, the problem of extracting the desired information can be facilitated, by way of example, in that a multi-dimensional problem can be transferred to a problem having fewer dimensions as indicated by the normalized preprocessed data stream 80a, 80b, 80c. As already mentioned above, the color normalization 88 may precede the luminance normalization 90, and vice versa.

In a subsequent step 92 a determination of a disturbance-reduced index element is carried out utilizing captured signals extracted from the data stream. As mentioned above, the determination can comprise methods of multivariate statistics. Further, the disturbance-reduced index element can be detected with consideration of the orientation of a predetermined index element, such as an approximately determined heart beat axis.

In a further subsequent step 94 detected characteristic index elements 50, 50' and 50" indicative of the desired information are projected to respective ones of the disturbance-reduced index elements determined in step 92 thereby eliminating noise-containing components of the characteristic index elements 50, 50' and 50" at least to a certain extent. In that way a data stream 82a, 82b, 82c highly indicative of the desired information can be created.

In an even further subsequent step 96 the desired information is extracted from the data stream 82a, 82b, and 82c. In other words, a temporal pulsation of the projected characteristic index elements is analyzed and extracted. In addition, a band pass filtering and/or Fourier domain analysis can be applied to the extracted data so as to further enhance the desired information in the noise-containing data. The band pass filtering can be depicted by a coordinate system provided with an amplitude axis 102 and a frequency axis 104. A signal form is represented therein some areas of which, the blocked zones 108a, 108b, are suppressed or even eliminated while a remaining bandwidth 106 can be enhanced. It can be envisaged that further analyses are applied to the data contained in the remaining bandwidth 106. In the remaining bandwidth a dominant frequency peak 110 can be determined which represents the desired information. Eventually, the output signal modified in this way can be made available at an output interface and distributed for further use.

By way of example, the present invention can be applied in the field of health care, e.g. unobtrusive remote patient monitoring, general surveillances, security monitoring and so-called lifestyle applications, such as fitness equipment, or the like.

To this end, it can be envisaged to extract and deliver detailed vital information, e.g. heart rate, heart rate variability, or even respiration rate. On the other hand, also information derived therefrom can be delivered, e.g., by way of example, the presence of a living being or of a mere picture thereof.

Further, it should be noted, that it can be envisaged to apply also a motion detection or image tracking for monitoring moving objects of interest. To this end, patterns of interest can be determined, e.g. highly-indicative face areas that can be tracked during capturing and subsequent processing. In this case, it could be further preferred if the averaging and normalization is done on a pattern level rather than a whole image frame level.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A remote monitoring device for extracting information from detected characteristic signals, comprising:
   a processor that:
      receives a data stream that includes a sequence of image frames derivable from electromagnetic radiation emitted or reflected by an object, the sequence of image frames comprising a continuous or discrete characteristic signal including physiological information, the physiological information being representative of at least one at least partially periodic vital signal,
      extracts the physiological information from the data stream by deriving a plurality of characteristic index elements from the data stream, the plurality of characteristic index elements being indicative of the physiological information and a disturbing signal component, wherein the plurality of characteristic index elements is associated with a signal space representative of characteristics of the electromagnetic radiation, the signal space comprising a predetermined index element having a set orientation indicative of a reference physiological information, the predetermined index element being at least approximately determinable by an upstream determination of respective reference values,
      converts the plurality of characteristic index elements by projecting them to a disturbance-reduced index element derived from a given orientation and length of the plurality of characteristic index elements, the disturbance-reduced index element having a distinct orientation in relation to a presumed orientation of the disturbing signal component, wherein the disturbance-reduced index element is determined by optimizing an expression with consideration of the orientation of the predetermined index element,
   wherein the processor determines the disturbance-reduced index element by;
      defining a dataset comprising a set of characteristic index element values derived from the set of characteristic index elements, and
      performing a transformation of the dataset to a coordinate system, wherein:
         a dominant component is aligned with an axis of the coordinate system and coincides with the disturbance-reduced index element, and
         the disturbance-reduced index element is determined by minimizing energy of the projected characteristic index elements over a temporal interval.

2. The device of claim 1, wherein the processor determines a temporal variation of the projected index element, and detects the at least one at least partially periodic vital signal represented by the physiological information.

3. The device of claim 2, wherein the processor compensates an angular offset between the projected index element and the predetermined index element having the set orientation.

4. The device of claim 2, wherein the processor filters the data stream and enhances a signal component at a bandwidth between 0.2 Hz and 10 Hz, preferably between 0.5 Hz and 3.5 Hz.

5. The device of claim 1, wherein the plurality of characteristic index elements is a set of difference vectors representing temporal variations of the continuous or discrete characteristic signal in the signal space.

6. The device of claim 1, including a camera adapted for capturing a signal within a signal space selected from the group consisting of RGB, sRGB, Rg chromaticity, HSV, HSL, CMYK, YPbPr, YCbCr, and xvYCC.

7. The device of claim 1, wherein the at least one at least partially periodic vital signal is selected from the group consisting of heart beat, respiration rate, and heart rate variability.

8. The device of claim 1, wherein the signal space is a normalized color space, wherein at least one degree of freedom is at least temporarily compensated by a normalization process.

9. The device of claim 1, wherein the processor transfers the data stream into the signal space by normalizing actual luminance values embedded in the data stream by applying a respective determined combination of primary colors to color-representative components of the data stream, and/or by normalizing the color intensity of the data stream by applying respective temporal mean values of the data stream to actual values of color-representative components thereof.

10. The device of claim 1, wherein the processor applies a weight function to determine the disturbance-reduced index element so as to converge the disturbance-reduced index element to the predetermined index element.

11. The device of claim 1, wherein the disturbance-reduced index element corresponds to a vector z that is determined by methods of multivariate statistics such that the expression $\|Sz\|^2 = (Sz)^T Sz = z^T(S^T S)z$ is minimized, wherein a matrix S comprises a stack of a plurality of difference row vectors $s^T$, and wherein a vector s corresponds to a characteristic index element.

12. The device of claim 1, including a sensor that detects the electromagnetic radiation within at least one particular wavelength range selected from the group consisting of visible light, infrared light, and ultraviolet radiation.

13. The device of claim 12, wherein the sensor includes a video camera.

14. A method for extracting information from detected characteristic signals, comprising:

receiving a data stream comprising a sequence of image frames derivable from electromagnetic radiation emitted or reflected by an object, the sequence of image frames comprising a continuous or discrete characteristic signal including physiological information, the physiological information being representative of at least one at least partially periodic vital signal, extracting the physiological information from the data stream by deriving a plurality of characteristic index elements from the data stream, the plurality of characteristic index elements being indicative of the physiological information and a disturbing signal component, wherein the plurality of characteristic index elements is associated with a signal space representative of characteristics of the electromagnetic radiation, the signal space comprising a predetermined index element having a set orientation indicative of a reference physiological information, the predetermined index element being at least approximately determinable by an upstream determination of respective reference values, converting the plurality of characteristic index elements by projecting them to a disturbance-reduced index element derived from a given orientation and length of the plurality of characteristic index elements, the disturbance-reduced index element having a distinct orientation in relation to a presumed orientation of the disturbing signal component, wherein the disturbance-reduced index element is determined by optimizing an expression with consideration of the orientation of the predetermined index element, wherein determining the disturbance-reduced index element comprises defining a dataset comprising a set of characteristic index element values and performing a transformation of the dataset to a coordinate system wherein a dominant component thereof is aligned with an axis of the coordinate system, wherein the dominant component coincides with the disturbance-reduced index element, and wherein the disturbance-reduced index element is determined by minimizing energy of the projected characteristic index elements over a temporal interval.

15. The method of claim 14, including detecting the electromagnetic radiation within at least one particular wavelength range selected from the group consisting of visible light, infrared light, and ultraviolet radiation.

16. The method of claim 15, including receiving the electromagnetic radiation from at least one of: a video camera and a video recording.

17. The method of claim 14, wherein the disturbance-reduced index element corresponds to a vector z that is determined by methods of multivariate statistics such that the expression $\|Sz\|^2 = (Sz)^T Sz = z^T(S^T S)z$ is minimized, wherein a matrix S comprises a stack of a plurality of difference row vectors $s^T$, and wherein a vector s corresponds to a characteristic index element.

18. The method of claim 14, including compensating an angular offset between the projected index element and the predetermined index element having the set orientation.

19. The method of claim 14, wherein the plurality of characteristic index elements is a set of difference vectors representing temporal variations of the continuous or discrete characteristic signal in the signal space.

20. A non-transitory computer readable medium that includes program code that, when executed, causes a processor to carry out the steps of the method as claimed in claim 14.

* * * * *